United States Patent [19]

Miller et al.

[11] Patent Number: 4,488,997
[45] Date of Patent: Dec. 18, 1984

[54] METHOD FOR THE PREPARATION OF HIGHER ANTIMONY TRICARBOXYLATES

[75] Inventors: Richard F. Miller; John Link, both of Humble, Tex.

[73] Assignee: Atlantic Richfield Company, Los Angeles, Calif.

[21] Appl. No.: 412,409

[22] Filed: Aug. 27, 1982

[51] Int. Cl.³ .............................................. C11C 1/00
[52] U.S. Cl. .................................... 260/414; 260/446
[58] Field of Search ................................ 260/446, 414

[56] References Cited

U.S. PATENT DOCUMENTS

| | | | |
|---|---|---|---|
| 2,996,528 | 8/1961 | Marks et al. | 260/446 |
| 3,031,425 | 4/1962 | Schoepfle | 260/446 X |
| 3,043,852 | 7/1962 | Mills | 260/446 X |
| 3,211,768 | 10/1965 | Considine | 260/446 X |
| 3,245,958 | 4/1966 | Hindersinn et al. | 260/446 X |
| 3,415,860 | 12/1968 | Thomas | 260/446 |
| 3,484,410 | 12/1969 | Lazarus et al. | 260/446 X |
| 3,714,077 | 1/1973 | Cobbledick et al. | 521/123 X |

OTHER PUBLICATIONS

Chemical Abstracts 77 102762g (1972).

*Primary Examiner*—Helen M. S. Sneed
*Attorney, Agent, or Firm*—C. R. Reap; D. M. Kozak; J. C. Martin, Jr.

[57] ABSTRACT

Antimony tricarboxylates of higher carboxylic acids can be prepared by
(a) reacting antimony oxide with an anhydride of a lower organic acid,
(b) reacting the product from (a) with at least one higher carboxylic acid at a temperature sufficient to vaporize volatile material and removing said volatile material, and
(c) recovering the antimony tricarboxylate of said higher carboxylic acid.

2 Claims, No Drawings

METHOD FOR THE PREPARATION OF HIGHER ANTIMONY TRICARBOXYLATES

FIELD OF THE INVENTION

Catalysts used in cracking hydrocarbons can become contaminated and poisoned by accumulation in the catalyst of metals such as nickel, vanadium, iron, copper and cobalt which are present in the hydrocarbon feedstocks. The detrimental effects of those metals can be mitigated and reversed by use of certain organo-antimony compounds as catalyst passivators. Among those organo-antimony compounds are antimony tricarboxylates. The present invention is an improved method of preparing antimony tricarboxylates.

BACKGROUND OF THE INVENTION

Certain antimony compounds are known to be used to treat those cracking catalysts conventionally employed in the catalytic cracking of hydrocarbons for the production of gasoline, motor fuel, blending components and light distillates. These conventional cracking catalysts generally contain silica, or silica-alumina. Such materials are frequently associated with zeolitic materials. These zeolitic materials can be naturally occurring, or they can be produced by conventional ion exchange methods such as to provide metallic ions which improve the activity of the catalyst.

While the presence of certain metals can be beneficial, the presence of others in the catalyst is detrimental. It is well known that verying amounts of metals such as nickel, vanadium and iron cause deterioration of the cracking catalyst during the cracking process. In fact, some oils contain these metals in such a high concentration that they cannot be economically cracked into gasoline and other fuels. The metals accumulate on the cracking catalyst and cause increased hydrogen production and coke laydown on the cracking catalyst, thereby adversely affecting the yield of desired products.

It has heretofore been proposed that those deleterious metals can be passivated by treating the contaminated catalyst with compounds containing antimony, tin, indium or bismuth (see U.S. Pat. No. 4,257,919). Antimony compounds are particularly useful as passivating agents and use of a wide variety of both organic and inorganic antimony compounds have been proposed for that purpose (see U.S. Pat. Nos. 4,111,845 and 4,153,536). Among the organic antimony compounds proposed are antimony tricarboxylates such as antimony tridodecanoate and antimony trioctadecanoate.

Prior art processes for antimony tricarboxylate preparation involve a direct reaction between antimony oxide and a carboxylic acid anhydride. Nerdel et al (J.Chem.Ber., 90, 598 (1957)) teach that antimony triacetate or antimony tribenzoate can be prepared by reacting antimony oxide with acetic anhydride or benzoic anhydride, respectively.

Ventura et al (U.S. Pat. No. 3,803,193) disclose reacting antimony tricarboxylates with alcohols to produce antimony trialkoxides. Ventura indicates that the tricarboxylate can be prepared by reacting antimony oxide with an organic acid anhydride directly or in some instances with an acid directly. The acid by-product of the tricarboxylate-alcohol reaction is taught to be neutralized with ammonia and removed as ammonium acetate solid.

The direct production of antimony tricarboxylates by the prior art methods of direct reaction between antimony oxide and the desired acid anhydride is not satisfactory for producing higher tricarboxylates because the higher anhydrides are not readily available and are synthetically prepared only with great difficulty. Accordingly, it is an object of the present invention to provide a process for preparation of higher tricarboxylates of antimony which uses readily available reactants and affords high yields of the desired tricarboxylates. It is another object of the invention to provide a synthetic method of preparation wherein the antimony tricarboxylate produced is substantially free of deletrious impurities without extensive purification and has a high level of thermal stability. These and other objects, aspects and advantages of the present invention will become apparent to those skilled in the art from the following description of the invention.

SUMMARY OF THE INVENTION

This invention relates to a highly effective and efficient method of preparing higher antimony tricarboxylates comprising the steps of (a) reacting antimony oxide with an anhydride of a lower organic acid, (b) reacting the product from (a) with at least one higher carboxylic acid at an elevated temperature sufficient to vaporize and remove volatile material, and (c) recovering the antimony tricarboxylate of said higher carboxylic acid.

DETAILED DESCRIPTION

According to the present invention, higher antimony tricarboxylates are produced from higher carboxylic acids by (a) reacting antimony oxide with an anhydride of a lower organic acid according to the following equation:

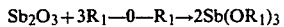

(b) reacting the product from (a) with at least one higher carboxylic acid at temperatures sufficiently high to vaporize and drive off volatile by-products of the reaction according to the equation

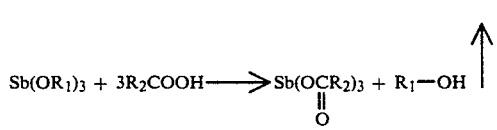

and (c) recovering the antimony tricarboxylate of said higher carboxylic acid.

The anhydrides of lower organic acids employed in step (a) are those anhydrides which are commercially available or readily prepared. Thus $R_1$ in the equation of step (a) has up to five carbon atoms. Preferably $R_1$ is alkanoyl of up to five carbon atoms and the lower organic acid anhydrides include acetic anhydride, propionic anhydride, butyric anhydride and pentanoic anhydride. Acetic anhydride is the especially preferred anhydride of a lower organic acid.

The reaction of step (a) can be conducted either with a solvent or without a solvent. When conducted with a solvent, the solvent must be inert to both reactants and the reaction product. A suitable solvent is a hydrocarbon having a boiling point of at least 120° C. and includes xylene, toluene, cumene, kerosene, and so forth.

Although an elevated temperature is used to increase reaction speed, the temperature of the step (a) reaction is not critical. A suitable temperature range is from 100° to 140° C. A temperature of about 120° C. results in a reaction time of about 3 to 4 hours between antimony oxide and acetic anhydride.

The reaction product from step (a) is reacted with one or more higher carboxylic acids. Higher carboxylic acids are those acids which have at least six carbon atoms. There is no criticality on the upper limit for the number of carbon atoms and is dictated only by practicality. Preferably, $R_2$ in the equation of step (b) is alkyl having from five to about 24 carbon atoms. More preferably, $R_2$ is cyclic, straight chain or branched chain alkyl having seven to eleven carbon atoms.

As illustrated above by the equation of the step (b) reaction, the reaction by-product of step (b) is the lower organic acid which corresponds to the lower acid anhydride employed in step (a). Thus when acetic anhydride is a reactant in step (a), acetic acid would be the by-product in step (b) when the higher carboxylic acid is reacted with the product of step (a). It is an important feature of this invention to remove the lower organic acid by-product from the reaction environment in order to have the reaction equilibrium favor formation of the antimony tricarboxylate of the higher carboxylic acids. Removal of the by-product lower organic acid is achieved by use of high temperatures, reduced pressure or a combination of those conditions.

In conducting the reaction of step (b), the higher carboxylic acid is mixed with the product of step (a) and the temperature of the mixture is increased until the by-product lower organic acid is evolved as a vapor. When acetic anhydride is a reactant in step (a), evolution of acetic acid vapor is observed in step (b) at a temperature of about 150° C. The temperature is continually increased until the reaction is substantially complete and the upper temperature can be about 300° C. When the reaction of step (b) is substantially complete, it is advantageous to reduce the pressure of the reaction in order to produce as complete removal as possible of by-product lower organic acid and the attendant completeness of reaction. Of course, it is possible to conduct the entirely of reaction step (b) under a sub-atmospheric pressure. The degree of pressure reduction is not particularly critical and its choice depends in part on the physical properties (e.g., boiling point) of the particular by-product species being removed. Thus a convenient pressure reduction can be easily determined by those having ordinary skill in the art.

The high temperature used to drive the reaction of step (b) to completeness also serves to eliminate excess and unreacted higher carboxylic acid which is also vaporized. At the completion of the reaction of step (b), the product remaining in the reactor is antimony tricarboxylate essentially free of deleterious impurities and can be used as a hydrocarbon cracking catalyst passivator without further purification. The recovery of the product therefore involves merely removing the antimony tricarboxylate of the higher carboxylic acid from the reactor after completion of step (b).

The following examples further illustrate specific embodiments of this invention but are not to be considered as limiting the invention to the specifics involved.

EXAMPLE 1

A three neck reaction flask was equipped with a stirrer, a heating mantle and a reflux condenser attached to a Dean-Stark trap. The flask was charged with 175 grams of antimony oxide, 212 grams of acetic anhydride and 125 grams of xylene. With stirring, the reaction mixture was heated to 120° C. and maintained at that temperature for 3 to 4 hours. Then, 663.9 grams of neodecanoic acid (technical grade) was added and the reaction mixture heated to 195° C. During the heating, xylene was removed by distillation and at approximately 155° C., the evolution of acetic acid was observed and was removed. Heating continued to 195° C. and when 195° C. was reached, the reaction mixture was cooled and the antimony trineodecanoate yield was determined to be 72.6%.

The technical grade neodecanoic acid used is a product of Exxon Chemicals and is a highly branched multi-isomer mixture combination with a typical hydrocarbon-type odor and melting point of less than −40° C. The structure of these isomers is generically represented by

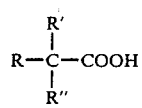

The sum of the carbon atoms for R, R' and R" in each isomer is eight. The Exxon technical grade neodecanoic acid employed has a typical isomer distribution as follows:

| | | |
|---|---|---|
| (i) | R = $CH_3$, R' = $CH_3$, R" = $C_6H_{13}$ | 31% |
| (ii) | R < $C_6H_{13}$, R' = $CH_3$, R" > $CH_3$ | 67% |
| (iii) | R < $C_6H_{13}$, R' > $CH_3$, R" > $CH_3$ | 2% |

Therefore, as the term is used herein, neodecanoic acid and neodecanoate esters include each of the several isomers of the technical grade material, either alone or in mixture.

EXAMPLE 2

The apparatus such as described in Example 1 was charged with 118.75 grams of antimony oxide, 265 grams of acetic anhydride and 100 grams of xylene. With stirring the reaction mixture was heated to 120° C. and maintained at that temperature for 3 to 4 hours. Then, a mixture of 274 grams of neodecanoic acid (technical grade) and 432 grams of 2-ethyl hexanoic acid was added and the reaction mixture heated to 240° C. During the heating from 120° C. to 240° C., nitrogen was bubbled through the reaction mixture by use of a subsurface nitrogen sparge. While the reaction mixture was heated from 120° C. to 240° C., xylene was removed by distillation and evolution of acetic acid was observed at about 150° to 155° C. and was removed. When the temperature of 240° C. was reached, the reaction mixture was cooled and the 264.41 grams of the antimony tricarboxylate was obtained with the yield calculated as 97.93%.

What is claimed is:

1. Antimony tricarboxylate having a mixture of neodecanoate ligands and 2-ethylhexanoate ligands prepared by the process comprising the steps of:
   (a) forming an antimony tricarboxylate by reacting antimony oxide with an anhydride of a lower organic acid at an elevated temperature,
   (b) reacting the product from (a) with neodecanoic acid and 2-ethylhexanoic acid at a temperature sufficiently high to replace substantially all of the lower organic acid radicals with neodecanoic acid and 2-ethylhexanoic acid radicals and remove the lower organic acid by-product and unreacted neodecanoic acid and 2-ethylhexanoic acid from the reaction zone, and (c) recovering the mixed antimony carboxylate of neodecanoic acid and 2-ethylhexanoic acid.

2. Antimony tricarboxylate prepared by the process of claim 1 having one neodecanoate ligand and two ligands of 2-ethylhexanoate.

* * * * *